United States Patent [19]
Scribner et al.

[11] Patent Number: 6,053,904
[45] Date of Patent: Apr. 25, 2000

[54] THIN WALL CATHETER INTRODUCER SYSTEM

[75] Inventors: Robert M. Scribner, 4697 Quail Creek La., Boulder, Colo. 80301; Kevin F. Browne, 1050 Lake Hollingsworth Dr., Lakeland, Fla. 33803

[73] Assignees: Robert M. Scribner, Los Altos, Calif.; Kevin F. Browne, Lakeland, Fla.

[21] Appl. No.: 08/628,767

[22] Filed: Apr. 5, 1996

[51] Int. Cl.⁷ .................................................. A61M 25/00
[52] U.S. Cl. ......................... 604/527; 604/104; 604/164; 604/525
[58] Field of Search .......................... 604/91, 104–106, 604/164, 280–282

[56] References Cited

U.S. PATENT DOCUMENTS

| | | | |
|---|---|---|---|
| 3,428,046 | 2/1969 | Remer et al. | 128/349 |
| 4,205,675 | 6/1980 | Vaillancourt | 128/214.4 |
| 4,230,123 | 10/1980 | Hawkins, Jr. | 128/658 |
| 4,274,408 | 6/1981 | Nimrod | 128/214.4 |
| 4,306,562 | 12/1981 | Osborne | 128/348 |
| 4,368,730 | 1/1983 | Sharrock | 604/158 |
| 4,417,886 | 11/1983 | Frankhouser et al. | 604/53 |
| 4,596,563 | 6/1986 | Pande | 604/264 |
| 4,705,511 | 11/1987 | Kocak | 604/282 |
| 4,955,862 | 9/1990 | Sepetka | 604/164 |
| 5,037,404 | 8/1991 | Gold et al. | 604/282 |
| 5,069,674 | 12/1991 | Fearnot et al. | 604/282 |
| 5,104,388 | 4/1992 | Quackenbush | 604/264 |
| 5,180,376 | 1/1993 | Fischell | 604/282 |
| 5,188,152 | 2/1993 | Ogawa | 138/129 |
| 5,205,830 | 4/1993 | Dassa et al. | 604/164 |
| 5,217,482 | 6/1993 | Keith | 606/194 |
| 5,312,360 | 5/1994 | Behl | 604/164 |
| 5,403,339 | 4/1995 | Nobuyoshi et al. | 606/194 |
| 5,423,773 | 6/1995 | Jimenez | 604/282 |
| 5,423,774 | 6/1995 | Fischell et al. | 604/282 |
| 5,507,092 | 4/1996 | Webster, Jr. | 604/282 |
| 5,533,987 | 7/1996 | Pray et al. | 604/280 |
| 5,538,513 | 7/1996 | Okajima | 604/282 |
| 5,554,139 | 9/1996 | Okajima | 604/282 |
| 5,569,200 | 10/1996 | Umeno et al. | 604/96 |
| 5,569,220 | 10/1996 | Webster, Jr. | 604/282 |
| 5,599,325 | 2/1997 | Ju et al. | 604/282 |
| 5,599,326 | 2/1997 | Carter | 604/282 |

*Primary Examiner*—Corrine McDermott
*Assistant Examiner*—N. Kent Gring
*Attorney, Agent, or Firm*—Sheridan Ross P.C.

[57] ABSTRACT

A thin wall catheter introducer system for penetrating through intravascular tissue walls and for facilitating the introduction of a catheter through the tissue wall is disclosed. In one embodiment, the system includes a sheath having a thin wall tubular member and a wire braid positioned about the tubular member for reinforcing the tubular member. The wire braid may include at least two intertwined wires wound about the tubular member. In another embodiment, the system includes a dilator for penetrating through an incision in an intravascular wall of a patient. The dilator may include a first tubular member and a reinforcing member which is positionable about the first tubular member to substantially inhibit buckling or kinking of the first tubular member. In yet another embodiment, the system includes a vascular access system for use in dilating and penetrating through an incision in an intravascular tissue wall and for facilitating introduction of a catheter into the incision.

46 Claims, 9 Drawing Sheets

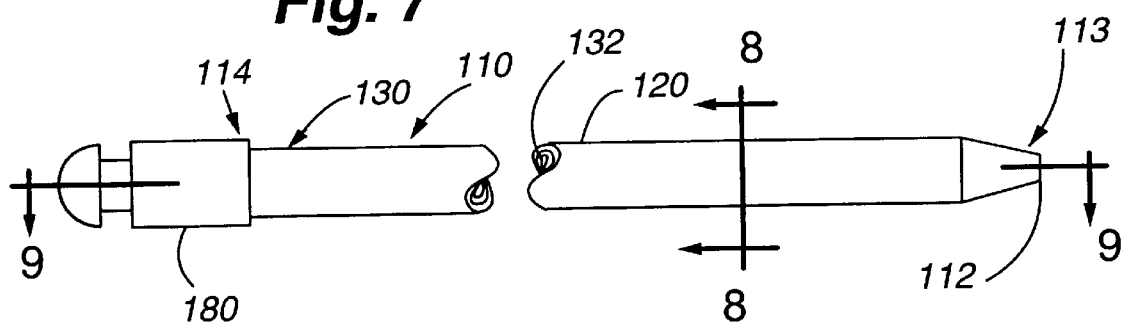
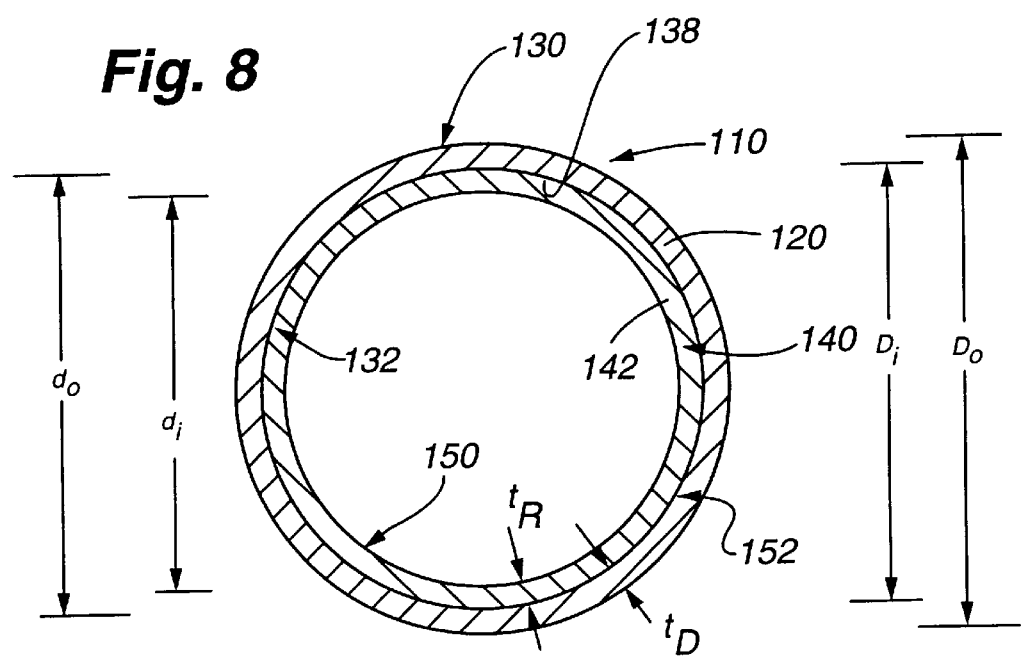

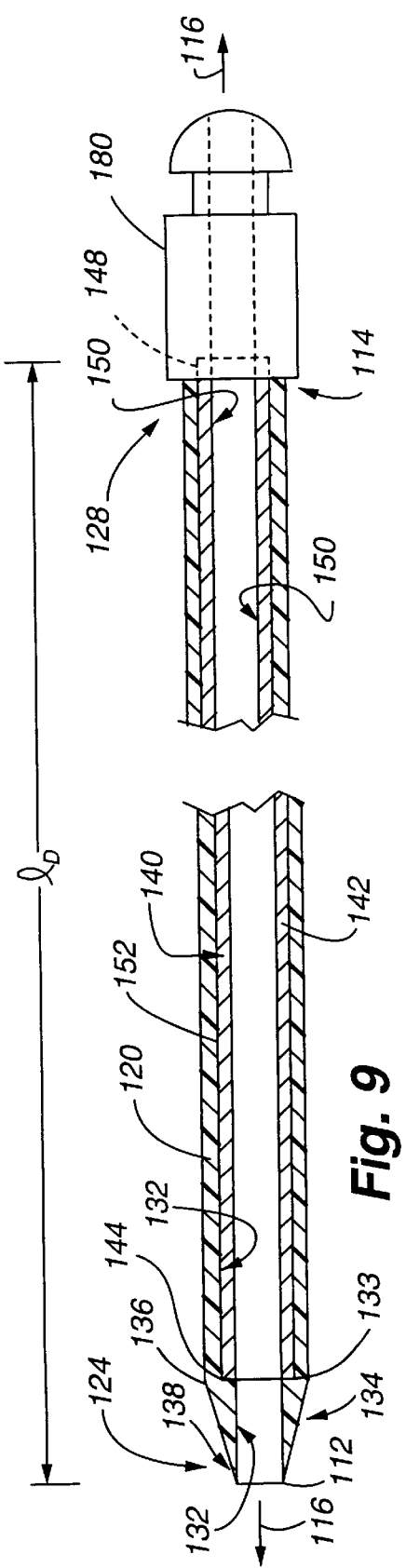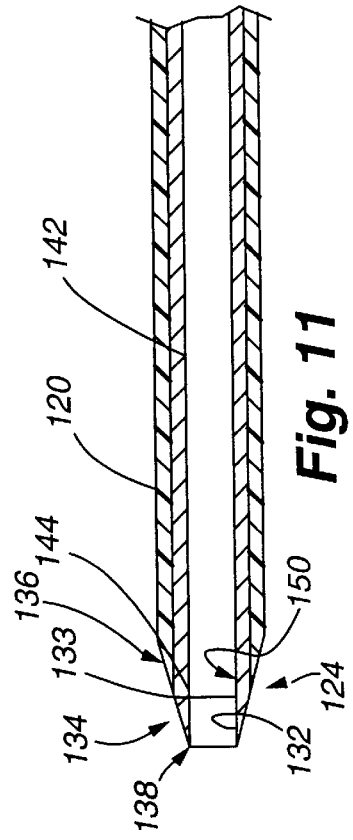

THIN WALL CATHETER INTRODUCER SYSTEM

FIELD OF THE INVENTION

The present invention relates to medical devices for introducing catheters through intravascular tissue walls, and, in particular, to a thin wall catheter introducer system for penetrating through intravascular tissue walls and facilitating the introduction of catheters through intravascular tissue walls.

BACKGROUND OF THE INVENTION

Catheter introducers are routinely used for access to the arterial system, providing a means of entry into the interior of an artery while inhibiting blood loss during catheter procedures. For example, catheter introducers are used for introduction of balloon angioplasty catheters into the femoral artery of a patient for access to the coronary arteries via the ascending and descending aorta to perform percutaneous transluminal coronary angioplasty.

Catheter introducers typically comprise an elongated tubular member open at both ends (e.g., a sheath), a tubular dilator slidably positionable within the sheath, and a guide wire slidably positionable within the dilator. Catheter introducers can be introduced into an artery utilizing a standard insertion procedure, such as the Seldinger technique. In the Seldinger technique, the artery wall is pierced by a stylet and cannula, the stylet is removed, the guide wire is inserted through the cannula, and the cannula is removed from the artery. In order to facilitate insertion of a sheath through the artery tissue wall, a dilator is inserted into the sheath to penetrate through hardened portions of the tissue wall, such as calcified regions of the artery or scar tissue resulting from prior sheath insertion. The sheath and dilator may then be introduced over the guide wire until the distal tip of the sheath is positioned within the artery. Introduction of the sheath and dilator into the artery should be accomplished quickly and efficiently, with minimal damage to the artery wall.

SUMMARY OF THE INVENTION

Accordingly, it is an object of the present invention to reduce damage to intravascular tissue wall by providing a sheath capable of accommodating a standard sized dilator while having a reduced outer diameter.

It is another object of the invention to inhibit buckling or kinking of a dilator during insertion and penetration of the dilator through scar tissue or hardened regions of an intravascular tissue wall.

It is a further object of the invention to provide a system for providing access to intravascular tissue which reduces damage to the intravascular tissue wall and resists buckling during insertion through an incision in the intravascular tissue wall.

In one aspect, the present invention is embodied in an assembly particularly adapted to facilitate introduction of a sheath through an incision in an intravascular tissue wall (e.g., a vein or an artery) of a patient, namely, a dilator. The sheath includes a tubular member having distal and proximal ends and defining a lumen extending therebetween for receiving the dilator and a wire braid positioned about at least a segment of the tubular member for reinforcing the tubular member. The wire braid may comprise at least two intertwined wires. In one embodiment, the wires of the wire braid are intertwined as at least a first of the wires is wound clockwise (e.g., helically clockwise) about the segment of the tubular member and at least a second of the wires is wound counter-clockwise (e.g., helically counter-clockwise) about the segment of the tubular member. For example, where the wire braid comprises sixteen wires, eight of the wires may be wound clockwise about the tubular member while the remaining eight may be wound counter-clockwise about the tubular member. In another embodiment, the wires of the wire braid may be interwoven to enhance the strength characteristics of the sheath, and specifically, to reinforce the tubular member. In this embodiment, at least a first of the wires of the wire braid overlays at least a second of the wires at a first position about the tubular member, and underlays the second of the wires at a second position about the tubular member. In this regard, the wires may be progressively or successively interwoven with each other in an overlaying-underlaying fashion as the wires are wound about the tubular member in a spiral-like (e.g., helical) manner. A distal portion of the wire braid is positionable below the skin line and/or through the incision in the tissue wall.

In one embodiment, while accommodating a standard size dilator, the sheath reduces damage to the intravascular tissue wall by providing a sheath having a reduced outer diameter. In this regard, the inner diameter of the sheath, as defined by the lumen of the tubular member, is sized to accommodate standard size dilators while the outer diameter of the sheath is reduced to minimize damage to the tissue wall. In this regard, the wall thickness of the sheath, as defined by the outer and inner diameters, is less than about 0.007 inches. In another embodiment, a ratio of the outer diameter to the inner diameter defines a first ratio. In a preferred embodiment, the first ratio is less than or equal to about 1.10.

In another aspect of the present invention, a sheath for use in introducing a catheter through an incision in an intravascular tissue wall of a patient is contemplated. The sheath may include a tubular means for receiving and being guided by a dilator through the incision. The tubular means comprises distal and proximal ends and defines a lumen extending therethrough, wherein the distal end of the tubular means is positionable beneath the skin line and/or through the incision. In one embodiment, where the distal and proximal ends define a tubular means length and an exterior surface of the tubular means defines a tubular means radius, the sheath has a column strength of at least about 0.2 lbs and a 30° bending stiffness of greater than about 0.12 lbs. The tubular means may comprise a tubular member and a wire braid having at least two intertwined wires positioned about the tubular member.

In another aspect, the present invention is embodied in an assembly for use in enlarging a puncture entry to an intravascular tissue wall of a patient. This assembly is particularly useful in penetrating through hardened (e.g., calcified) regions and scar tissue about the incision. The assembly, namely, a dilator, includes a first tubular member having distal and proximal portions and defining a lumen extending therethrough, and a reinforcing member positionable within the first tubular member. For purposes of providing axial support to the first tubular member and for enhancing the column strength and resistance to buckling of the first tubular member, the reinforcing member may extend between the distal and proximal portions of the first tubular member. In order to penetrate through and/or expand the incision (e.g., dilate the incision) while substantially inhibiting buckling or kinking of the first tubular member, distal portions of the first tubular member and the reinforcing member are positionable below the skin line and/or through the incision in the intravascular tissue wall.

A wall thickness of the first tubular member is defined by an exterior surface of the first tubular member and the lumen. A wall thickness of the reinforcing member comprising a second tubular member is defined by an exterior surface of the second tubular member and a bore defined by the second tubular member. A ratio of wall thicknesses of the first tubular member to the second tubular member may be between about 7 and about 90. Preferably, the ratio of wall thicknesses of the first tubular member to the second tubular member is less than about 50.

In yet another aspect, the present invention involves a dilator for use in penetrating through an incision in an intravascular tissue wall. The dilator includes a tubular means. For purposes of penetrating through and dilating the incision, a distal portion of the tubular means is positionable below the skin line and/or through the incision. Furthermore, the tubular means has an exterior surface and distal and proximal portions of the tubular means define a tubular means length. The exterior surface of the tubular means defines a tubular means radius. In one aspect, the tubular means has a column strength of at least about 0.4 lbs and a 30° bending stiffness of greater than about 0.2 lbs. Preferably, the tubular means has a column strength of at least between about 0.4 lbs. and about 2.5 lbs. and a 30° bending stiffness of between about 0.2 lbs. and about 2.0 lbs.

In another aspect, the present invention provides a vascular access system for use in penetrating an incision in an intravascular tissue wall of a patient and for facilitating the introduction of a catheter through the incision in the tissue wall. The vascular access system may include a sheath for receiving and advancing with a dilator through the incision in the tissue wall. For purposes of penetrating through the incision and dilating the incision, a distal portion of the dilator is positionable through the incision in the tissue wall, which provides for positioning of a distal portion of the sheath through the incision. In one aspect, a ratio of the outer diameter of the sheath, as defined by the exterior surface of the sheath, to the outer diameter of the dilator, as defined by the exterior surface of the dilator, is less than about 1.20. Preferably, the ratio of outer diameters of the sheath and dilator is between about 1.07 and about 1.18.

In another embodiment of the vascular access system, the sheath comprises a first tubular member defining a lumen extending therethrough capable of receiving the dilator therein. For purposes of reinforcing the sheath, which has a wall thickness of less than about 0.007 inches, the sheath may further comprise a wire braid positioned about at least a segment of the first tubular member. The wire braid includes at least two intertwined wires, which yields a sheath having a column strength of at least about 0.2 lbs.

In another embodiment of the vascular access system, the dilator comprises a second tubular member defining a bore therethrough for receiving a reinforcing member positionable therein to provide axial support to the second tubular member (e.g., provide increased column strength and resistance to buckling). In this regard, the reinforcing member substantially inhibits buckling and kinking of the second tubular member during insertion of the distal portion of the dilator through the incision in the tissue wall. The reinforcing member may comprise a third tubular member, a distal portion of which may extend into a distal, tapered portion of the second tubular member to reinforce the tapered portion of the second tubular member. A ratio of the outer diameter of the second tubular member to the outer diameter of the reinforcing member may be less than about 7.5. Such dilators may have a column strength of at least about 0.4 lbs.

In yet another aspect, the present invention is embodied in a method for penetrating through and dilating an incision in an intravascular tissue wall. The method includes the steps of positioning a distal portion of a dilator through the incision to facilitate introduction of a sheath, distal the intravascular tissue wall, and positioning a distal portion of an introducer sheath through the incision, distal the intravascular tissue wall, wherein the step of positioning the distal portion of the sheath comprises advancing a distal portion of a wire braid wound about the sheath below the skin line and through the incision. In one embodiment, where the sheath comprises a first tubular member and the dilator comprises a second tubular member and a reinforcing member positioned within the second tubular member, the step of positioning the distal portion of the dilator may further comprise the step of advancing a distal portion of the reinforcing member below the skin line and/or through the incision.

In another embodiment, the method may further comprise the step of inserting a distal end of a guide wire through the incision. In this regard, the steps of positioning the distal portions of the sheath and dilator through the incision may comprise the steps of advancing at least the distal portions of the sheath and dilator over the guide wire, toward the distal end of the guide wire. In another embodiment, the steps of advancing the distal portions of the sheath and dilator comprise slidably engaging the distal portions of the sheath and dilator with the guide wire to bend at least the distal portions of the sheath and dilator to follow the guide wire distal (e.g., below) the skin line and/or through the incision.

BRIEF DESCRIPTION OF THE DRAWINGS

FIG. 7 is a side view of reinforced dilator embodying principles of the present invention;

FIG. 8 is a section view of FIG. 7 taken along line 8—8;

FIG. 9 is a longitudinal section taken along line 9—9 in FIG. 7;

FIG. 10 is a longitudinal section view of another embodiment of the dilator illustrated in FIG. 7;

FIG. 11 is a longitudinal section view of yet another embodiment of the dilator illustrated in FIG. 7;

DETAILED DESCRIPTION

FIGS. 1–14 illustrate a thin wall catheter introducer system embodying the features of the present invention. For ease of description, in the discussion of the invention, the term "distal" refers to the direction toward the patient while the term "proximal" refers to the direction away from the patient.

Figure 1:
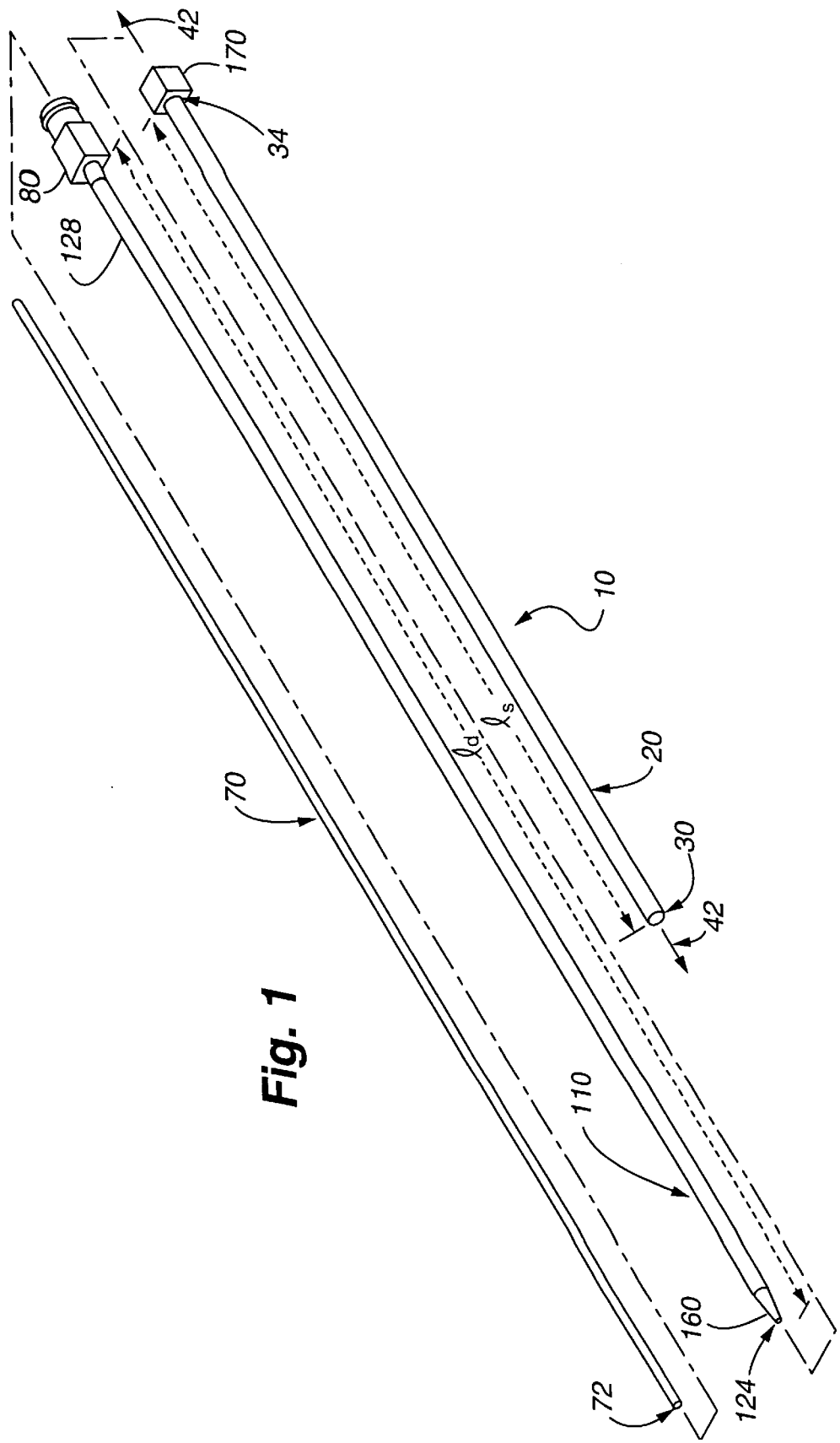
FIG. 1 is an exploded assembly view of an apparatus embodying the principles of the present invention.

Referring to FIG. 1, the catheter introducer system 10 generally comprises a sheath 20 (e.g., introducer) and a dilator 110 for penetrating through the tissue wall of a patient and for facilitating the introduction of a catheter (not shown) into the tissue wall (e.g., artery). In this regard, the sheath 20 may be used to receive a dilator 110, which penetrates through an incision in an artery wall. Once the dilator 110 has penetrated through the artery wall, especially hardened (e.g., calcified) portions of the artery wall, the dilator 110 may be withdrawn from the sheath 20 and the sheath 20 may be used for introducing a catheter into the artery wall.

In one embodiment of the sheath 20, illustrated in FIGS. 2–6, in order to provide for introduction of current intravascular catheters through the sheath 20 and into the artery through a hole in the artery having a reduced diameter (for a given catheter), which thereby minimizes damage to the artery, the sheath 20 comprises a tubular member 26 of reduced outer diameter ($D_o$) and wall thickness ($t_s$). For example, in standard six (6) French size sheaths, the outside diameter of the sheath is 0.101 inches and the inner diameter ($D_i$) of the sheath, as defined by a lumen extending through the sheath, is 0.085 inches. Such sheaths have a wall thickness of 0.008 inches and are configured to accommodate a catheter having a diameter up to 6 French (0.078 inches). In one embodiment of the sheath 20 according to the principles of the present invention, a thin wall sheath 20 capable of receiving catheters up to size 6 French in diameter (0.078 inches) may have an outer diameter of about 0.091 and an inner diameter of about 0.082 inches, and a wall thickness of about 0.0045 inches. In this regard, thin wall sheaths 20 configured according to the principles of the present invention minimize damage to the artery while providing access to the artery via standard size catheters. In addition, for a standard diameter hole in the tissue wall (e.g., artery), the sheath 20 may allow use of a larger diameter catheter.

In one embodiment of the invention, illustrated in FIGS. 2–6, the sheath 20 comprises a tubular member 26 having distal and proximal ends 30, 34 and a lumen 38 extending therethrough, the distal end 30 being positionable through a hole 16 in the intravascular tissue wall 18. An outer diameter ($D_o$) of the sheath 20 is defined by an exterior surface 46 of the sheath 20 and an inner diameter ($D_i$) of the sheath 20 is defined by the lumen 38. The tubular member 26 of the sheath 20 may comprise a polymeric material selected from the group consisting of polyurethane, polyethylene, PVC, nylon, Pebax, Teflon or other plastic materials. In a preferred embodiment, the tubular member 26 comprises polyethylene. In addition, to inhibit damaging tissue, the tubular member 26 should be relatively soft (e.g., having a shore D hardness of between about 30 and about 70).

For purposes of guiding a catheter through the hole 16, the distal end 30 of the sheath 20 is positionable through the hole 16. In order to facilitate insertion of the distal end 30 of the sheath 20 through the hole 16, the outer diameter of the sheath 20 at the distal end 30 is formed with a radius.

Figure 6:
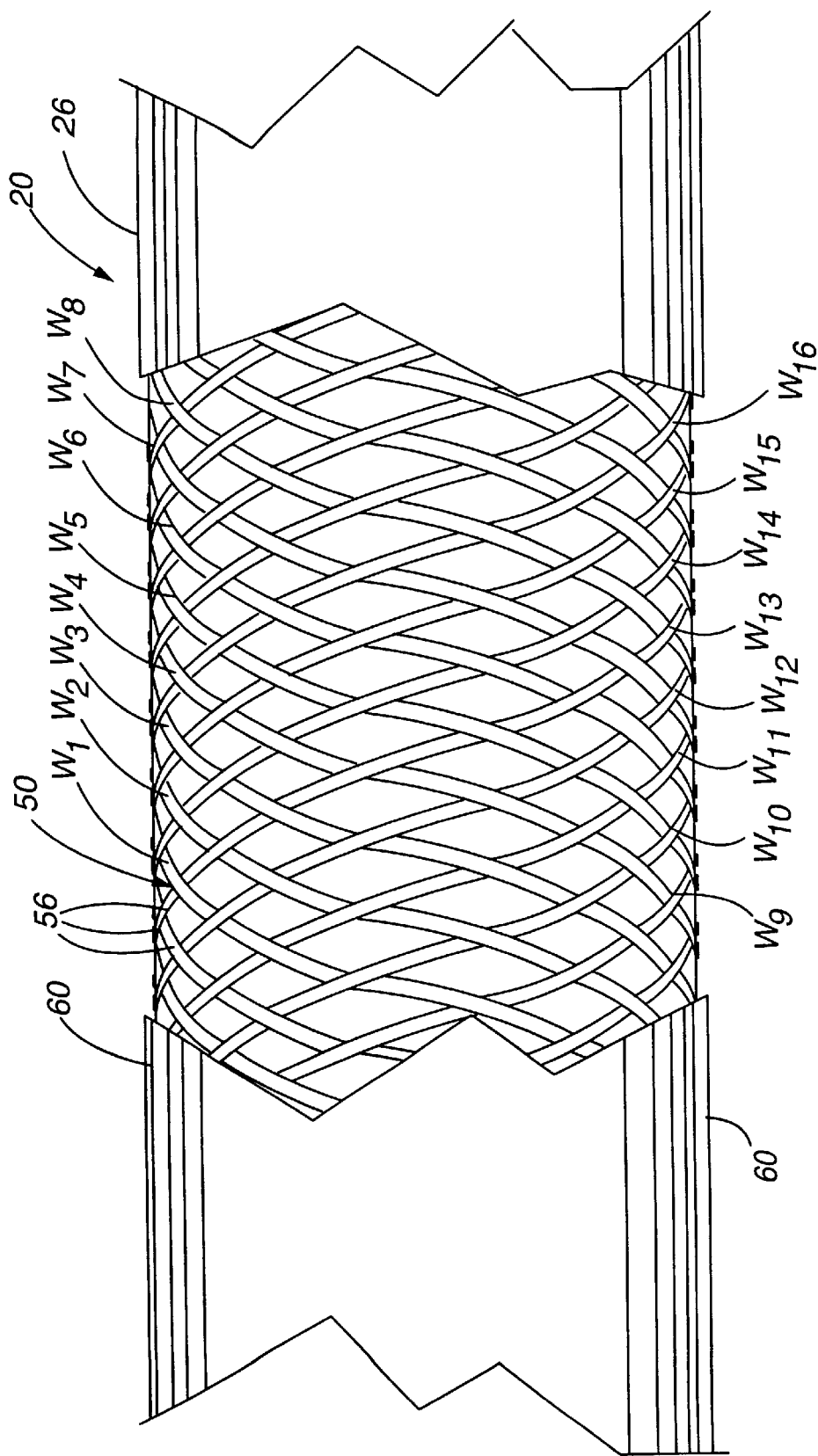
FIG. 6 is a side view of the sheath showing the cutaway section illustrated in FIG. 2.

The sheath 20 may further comprise a wire braid 50 positioned about a length of the tubular member 26 for reinforcing the tubular member 26 along its longitudinal axis 42. In this regard, the wire braid 50 generally inhibits kinking or buckling of the tubular member 26 as axially-directed forces are applied at the proximal end 34 of the sheath 20 to insert the distal end 30 of the sheath 20 into and through the hole 16 of the artery 18. In one embodiment, the wire braid 50 may be positioned along a length of the tubular member 26, substantially between the exterior surface 46 and the lumen 38 of the sheath 20. In this regard, the wire braid 50 may be substantially held in place by enclosing the wire braid 50 within the tubular member 26. As shown in FIG. 6, the wire braid 50 may be positioned within the wall of the tubular member 26, under an outer layer 60 of the tubular member 26. Alternatively, the wire braid 50 may be positioned on the exterior surface 46 of the sheath 20, or about the lumen 38.

As shown in FIGS. 2–6, the wire braid 50 comprises a plurality of intertwined wires 56 wound about a length of the tubular member 26. In order to sufficiently reinforce the tubular member 26, the wires 56 may comprise a material selected from the group consisting of stainless steel, nitinol, other metals, polymers or fabrics. The wires 56 may have a dimension (e.g., diameter, length, width etc.) of between about 0.0005 inches and about 0.0025. In addition, the wires 56 may have a cross-section selected from the group consisting of rectangles, circles, squares, triangles, ellipses and multiple filament composites. In a one embodiment, at least one of the wires 56 has a rectangular cross-section measuring between about 0.0005 inches by about 0.0025 inches.

For purposes of providing the tubular member 26 with increased column strength and resistance to buckling, the wire braid 50 comprises at least two intertwined wires 56. For ease of manufacture, the wire braid 50 comprises an even number of wires (e.g., 16), although the wire braid 50 may comprise an odd number of wires (e.g., 3). In this regard, the wire braid 50 may comprise a plurality of wires 56 (e.g., 8, 10, 12, 14, 16, 18, 20, 32 etc.). In one embodiment, illustrated in FIG. 6, the wire braid 50 comprises a plurality of wires 56, wherein at least a first of the wires 56 may be wound about the tubular member 26 in a clockwise direction and at least a second of the wires 56 may be wound about the tubular member 26 in a counter-clockwise direction. For example, where the wire braid 50 comprises sixteen wires 56, eight wires 56 may be wound in a spiral-like manner (e.g. helical) about the tubular member 26 in a clockwise direction and eight wires 56 may be wound in a spiral-like manner about the tubular member 26 in a counter-clockwise direction.

In one embodiment of the sheath 20, the plurality of wires 56 wound about the tubular member 26 are intertwined, as shown in FIG. 6. In this regard, the wires 56 may be wound about the tubular member 26 in an interlaced or woven manner. In this regard, at least a first of the wires 56 may overlay at least a second of the wires at a first position about the tubular member 26, and may underlay the second wire at a second position about the tubular member 26. For example, where the wire braid 50 comprises sixteen wires 56, eight of which are wound about the tubular member 26 in a clockwise direction (e.g., $W_{1-8}$) and eight of which are wound about the tubular member 26 in a counter-clockwise direction (e.g., $W_{9-16}$), at least a first clockwise wound wire 56 (e.g., $W_3$) may pass over (e.g., overlay) at least one counter-clockwise wound wire 56 (e.g., $W_{15}$) and under (e.g., underlay) at least one counter-clockwise wound wire 56 (e.g., $W_{14}$) in a repeating or successive manner along the length of the tubular member 26. Similarly, at least a first counter-clockwise wound wire (e.g., $W_9$) may pass over (e.g., overlay) at least one clockwise wound wire 56 (e.g., $W_2$) and under (e.g., underlay) at least one clockwise wound wire 56 (e.g., $W_1$) in a repeating or successive manner. It is believed that such intertwining of the wires 56 about the tubular member 26 further enhances the column strength and/or the resistance to buckling of the tubular member 26. In addition, the spacing of the wound wires 56 of the wire braid 50 about the tubular member 26 may be between about 5 pic/inch and about 80 pic/inch, and preferably, between about 20 pic/inch and about 50 pic/inch.

In another embodiment (not shown), where the wire braid 50 comprises sixteen wires 56, eight of which are wound in a spiral-like manner about the tubular member 26 in a clockwise direction and eight of which are wound in a spiral-like manner about the tubular member 26 in a counter-clockwise direction, a first clockwise wound wire 56 may pass over (e.g., overlay) two counter-clockwise wound wires 56 and under (e.g., underlay) two counter-clockwise wound wires 56 in a repeating or successive manner along the length of the tubular member 26. Similarly, first counter-clockwise wound wire may pass over (e.g., overlay) two clockwise wound wires 56 and under (e.g., underlay) two clockwise wound wires 56 in a repeating or successive manner along the length of the tubular member 26.

In order to accommodate catheters of varying sizes (e.g., 4-24 French) while minimizing damage to tissue (e.g., artery walls), for such standard size catheters, a ratio of the outer diameter of the sheath 20 to the inner diameter of the sheath 20 is less than about 1.10. More preferably, the ratio of outer diameter to inner diameter for the sheath 20 is between about 1.07 and about 1.10. A wall thickness ($t_s$) of the sheath 20, defined by the outer diameter and the inner diameter of the sheath 20, is less than about 0.007 inches. In this regard, a sheath 20 fabricated according to the principles of the present invention has a 30° bending stiffness of at least about 0.2 lbs. and a column strength of at least about 0.2 lbs. Furthermore, the sheath 20 may have a resistance to buckling of at least about 0.2 lbs.

Figure 2:
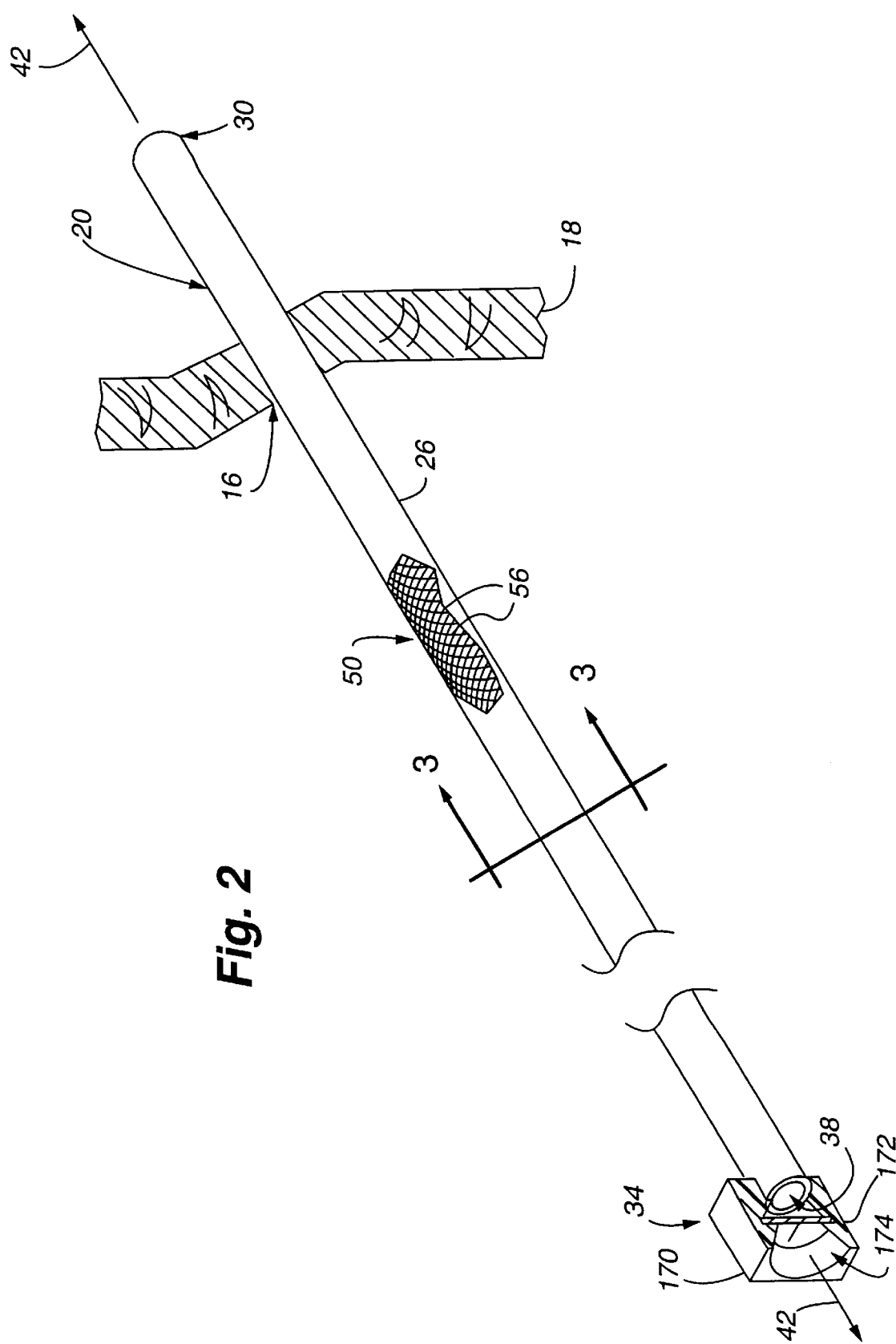
FIG. 2 is a perspective view of an introducer sheath inserted into an incision in an intravascular tissue wall with a cutaway view of the sheath showing a wire braid.
Figures 3, 4, 5:
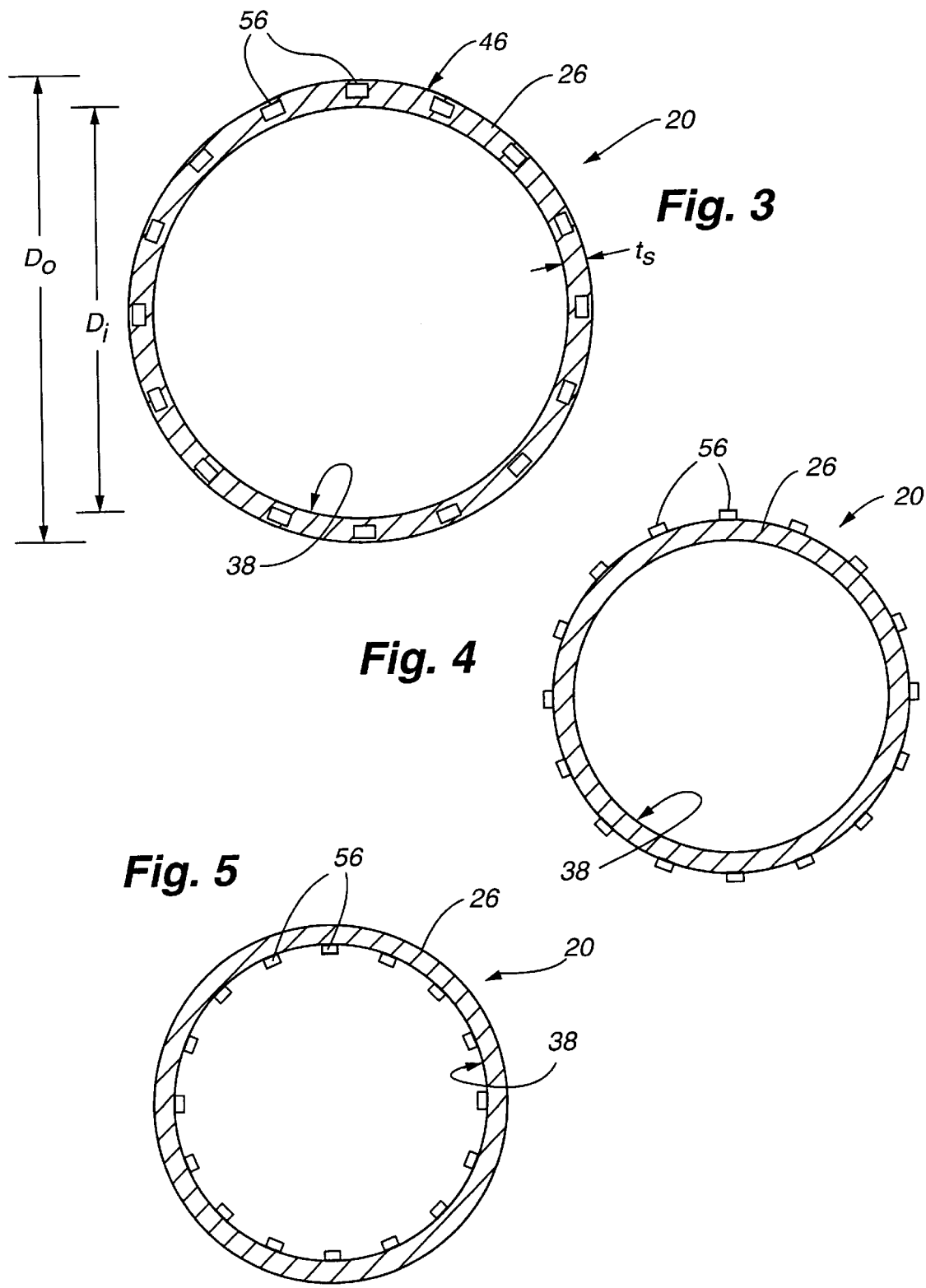
FIG. 3 is a section view taken along line 3—3 in FIG. 2.
FIG. 4 is a section view of another embodiment of the introducer sheath.
FIG. 5 is a section view of yet another embodiment of the introducer sheath.

As shown in FIG. 2, the sheath 20 may further include a hub 170 positioned at the proximal end 34 of the sheath 20 for substantially inhibiting leakage of blood as the distal end 30 of the sheath 20 is positioned (e.g., inserted) through the hole 16 in the intravascular tissue wall 18. In one embodiment, the adapter 170 is a hemostasis valve adapter which has a hemostasis valve 172 capable of receiving a dilator through an opening 174 (e.g., slit). The adapter 170 may comprise a material selected from the group consisting of pebax, polyethylene, nylon, polyurethane, PVC or similar polymer materials.

FIGS. 7–11 illustrate another aspect of the invention. Referring to FIG. 7, the apparatus for use in penetrating an intravascular tissue wall (e.g., artery) of a patient comprises a dilator 110. Dilators 110 fabricated according to the principles of the present invention are especially useful in penetrating through hardened portions of tissue, such as scar tissue and calcified regions of an artery. In this regard, the dilator 110 comprises a first tubular member 120. The first tubular member 120 may comprise a polymeric material selected from the group consisting of pebax, polyurethane, polyethylene, PVC, Teflon or other plastic materials. In a preferred embodiment, the first tubular member 120 comprises polyethylene. In addition, the first tubular member 120 may have a shore D hardness of between about 30 and about 80.

In one embodiment, illustrated in FIGS. 7–9, an exterior surface 130 of the first tubular member 120 of the dilator 110 defines an outer diameter ($D_o$) of the dilator 110. Since the dilator 110 is typically inserted through a lumen of an introducer or sheath to dilate the hole in the tissue wall to facilitate insertion of the sheath or a catheter, the outer diameter of the dilator 110 is less than or substantially equal to the inner diameter of the introducer lumen and may generally correspond to the outer diameter of a compatible catheter to be inserted through the introducer lumen and hole in the tissue wall. For example, for an introducer or sheath lumen which is compatible with a six French dilator, the outer diameter of the dilator 110 may be substantially equal to 0.078 inches.

The first tubular member 120 also comprises a lumen 132 which extends between the distal and proximal ends 124, 128 of the first tubular member 120. The wall thickness of the dilator 110, as defined by the exterior surface 130 and the lumen 132, may be less than about 0.1345 inches. The lumen 132 defines an inner diameter ($D_i$) of the first tubular member 120, which is sized and configured to accommodate a guide wire 70 receivable therethrough. For example, in instances where a 5-10 French catheter will be used for providing access to an artery, the guide wire 70 may have an outer diameter of about 0.038 inches. In this regard, the inner diameter of the first tubular member 120 should be large enough such that the dilator easily slides over the guide wire 70. The inner diameter of the first tubular member 120 should thus measure at least 0.038 inches where a 5-10 French catheter will be used.

For purposes of enhancing penetration through hardened tissue, a distal portion 124 of the first tubular member 120 may comprise a tapered segment 134. In this regard, the outer diameter of the first tubular member 120 at the distal end 112 of the dilator 110 is less than the outer diameter of the dilator at a point proximal the distal portion 124. The tapered segment 134 may comprise first and second portions, 136, 138. The outer diameter of the tapered segment 134 at the first portion 136 is greater than the outer diameter of the tapered segment 134 at the second portion 138, wherein the second portion 138 corresponds to the distal end 112 of the dilator 110. The tapered segment 134 may be tapered at an angle between about 1° and about 10°, relative to a longitudinal axis 116 of the dilator 110.

The dilator 110 may further comprise a reinforcing member 140 which is positionable about the first tubular member 120 to provide axial support to the first tubular member 120 as forces are applied on a proximal end 114 of the dilator 110 to insert a distal end 112 of the dilator 110 through the tissue wall via the Seldinger technique. The reinforced dilator 110 will thus resist bending perpendicular to the longitudinal axis 116 of the dilator 110 and resist kinking or collapsing when the distal end 112 of the dilator 110 contacts hardened or calcified subcutaneous tissue upon insertion through the tissue wall. For purposes of providing a reinforced dilator 110 which is compatible with standard size catheters and introducers, dilators 110 fabricated according to the principles of the present invention provide increased column strength and resistance to buckling without increases in wall thickness and/or outer diameter.

The reinforcing member 140 may comprise a second tubular member 142 having distal and proximal ends 144, 148 and a bore 150 (e.g., lumen) extending therethrough. The outer diameter ($d_o$) of the second tubular member 142 is defined by an exterior surface 152 of the second tubular member 142 and an inner diameter ($d_i$) of the second tubular member 142 is defined by the bore 150. A wall thickness ($t_R$) of the second tubular member 152, as defined by the outer and inner diameters of the second tubular member 142, may range from about 0.0005 inches to about 0.020 inches, and more preferably, between about 0.0005 inches and about 0.004 inches. The second tubular member 142 may comprise a material selected from the group consisting of stainless steel, other metals, liquid crystal polymer, or other composite structures. For purposes of enhancing the column strength and resistance to buckling of the dilator 110, the second tubular member 142 preferably comprises stainless steel.

In one embodiment, for purposes of reinforcing the first tubular member 120 while accommodating use of corresponding size catheters, the second tubular member 142 is positionable about the lumen 132 of the first tubular member 120. In this configuration, the outer and inner diameters of the second tubular member 142 may be selected to accommodate positioning within the lumen 132 of the first tubular member 120 while accommodating positioning over the guide wire 170 which passes therethrough. In addition, the lumen 132 of the first tubular member 120 should have a diameter sufficient and/or be configured to accommodate positioning of the second tubular member 142 therein.

Figure 12:
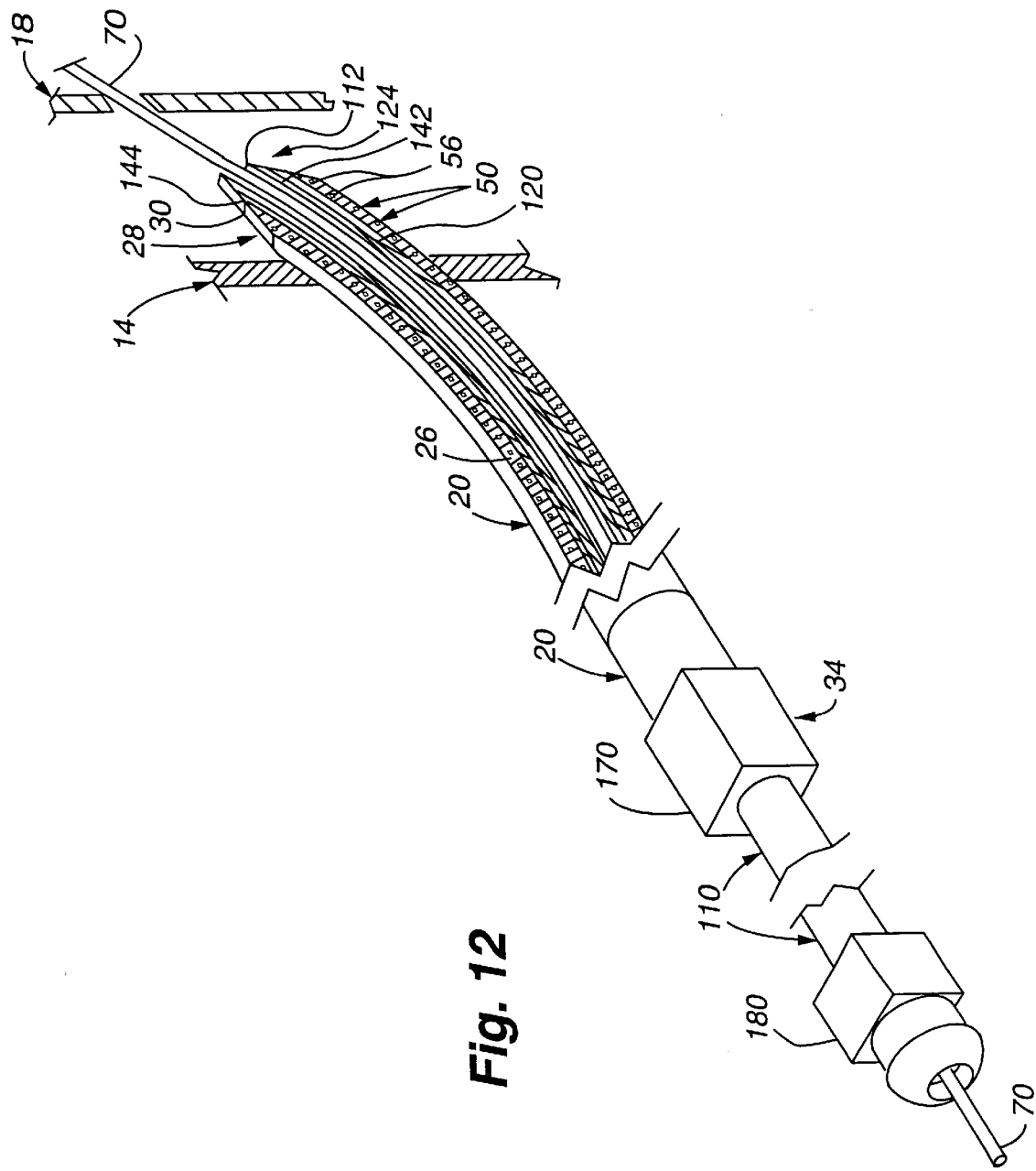
FIG. 12 is a longitudinal section view of the dilator being inserted into an incision in the intravascular tissue wall, below the skin line.
Figure 13:
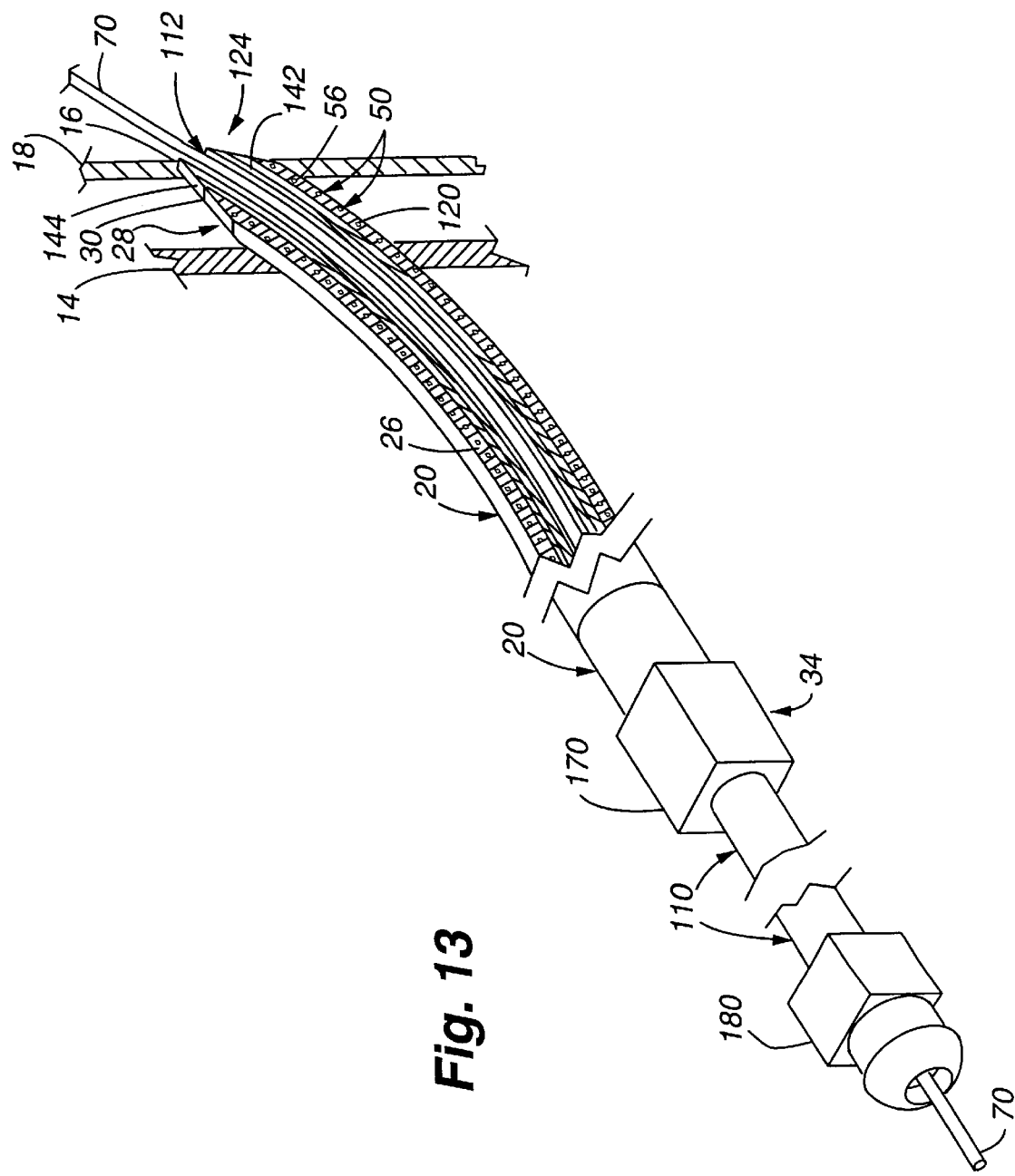
FIG. 13 is a section view of FIG. 12 with the distal end of the reinforced dilator inserted through the incision.
Figure 14:
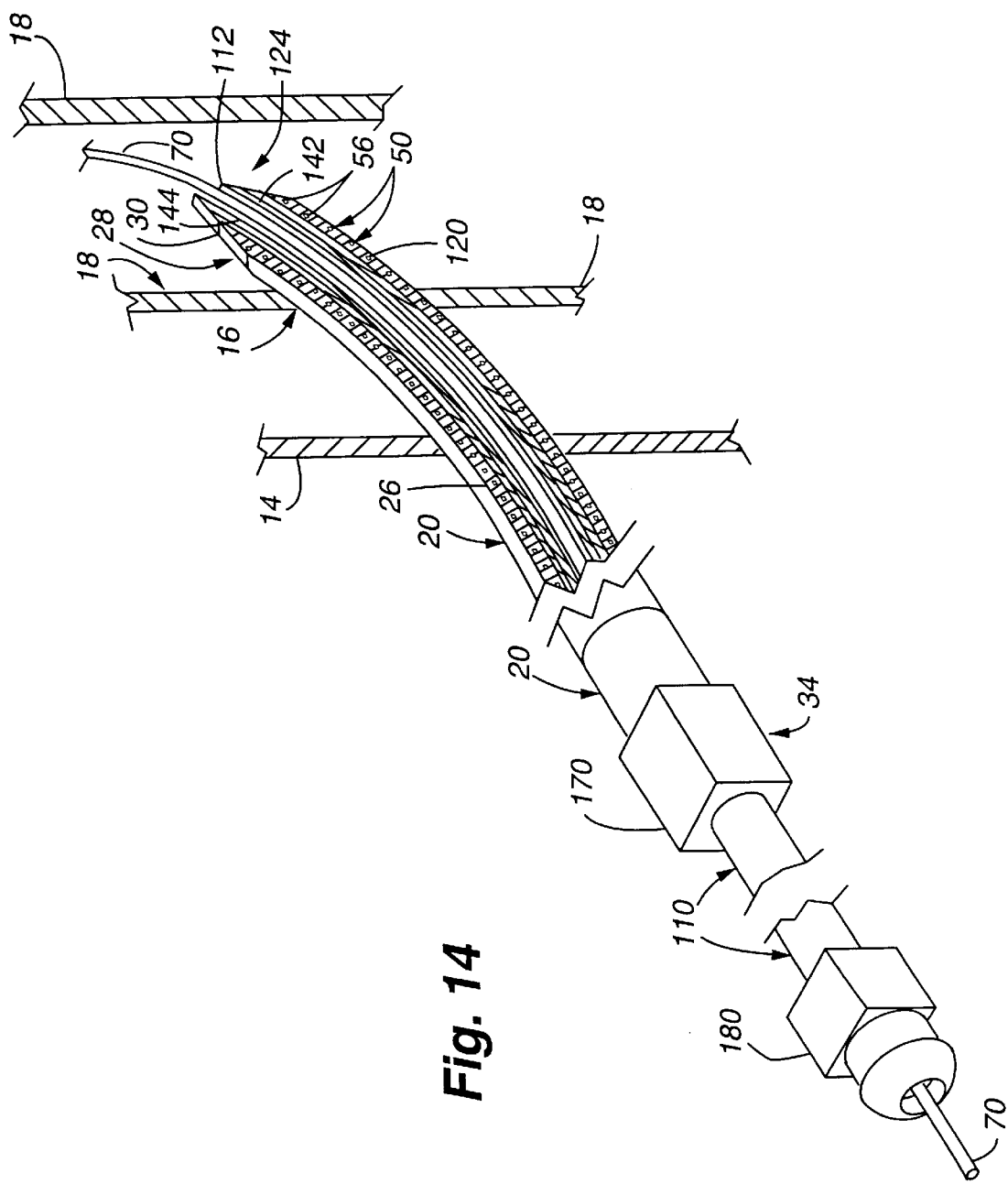
FIG. 14 is the section view of FIG. 12 showing the distal ends of the dilator and the sheath inserted through the incision in the intravascular tissue wall.

For example, for a reinforced dilator 110 fabricated according to the principles of the present invention and compatible with standard size six French (6F) catheters, the outer diameter of the first tubular member 120 may be approximately 0.078 inches. Furthermore, the inner diameter of the first tubular member 120 (i.e., lumen 132) must be large enough to accommodate the second tubular member 142, which, in turn, should be sized to accommodate a guide wire 70, which may, for 6F catheters, have an outer diameter of 0.038 inches. In this regard, and as illustrated in FIGS. 12–14, the first tubular member 120, and specifically, the lumen 132 therethrough, may comprise a cylindrical channel 133 for positioning of the second tubular member 142. For compatibility with 6F catheters and/or introducers, the channel 133 may have a diameter of about 0.045 inches. The channel 133 of the first tubular member 120 may thus accommodate positioning of the second tubular member 142 having an outer diameter of about 0.043 inches and an inner diameter of about 0.040 inches, which yields a wall thickness of the second tubular member 142 of about 0.015 inches. As such, dilators 110 fabricated according to the principles of the present invention are reinforced to resist buckling and kinking and are compatible with standard size catheters and introducers (e.g., 6F) and guide wires.

In order to substantially inhibit kinking or buckling of the dilator 110, and specifically, the first tubular member 120, the second tubular member 142 may be configured to extend between the distal and proximal portions 124, 128 of the first tubular member 120. In one embodiment, for purposes of reinforcing the tapered segment 134 of the first tubular member 120, and especially since the tapered segment 134 must penetrate through calcified tissue, the tapered segment 134 is reinforced by a portion of the second tubular member 142. In this embodiment, the distal end 144 of the second tubular member 142 may extend into the tapered segment 134, between the first and second portions 136, 138 of the tapered segment 134, or alternatively, up to the second portion 138 of the tapered segment 134, as illustrated in FIG. 10. In another embodiment, the distal end 144 of the second tubular member 142 may extend into the distal portion 124 of the first tubular member 120, as illustrated in FIG. 11.

For purposes of translating forces applied at the proximal end 114 of the dilator 110 during insertion of the dilator 110 into the tissue wall to the distal end 112 of the dilator 110, and providing resistance to buckling and increased column strength to the dilator 110, and specifically, along a length of the first tubular member 120, the proximal end 148 of the second tubular member 142 extends at least to the proximal end 128 of the first tubular member. In one embodiment, wherein the dilator 110 further comprises a luer fitting 180, illustrated in FIG. 9, the proximal end 148 of the second tubular member 142 extends beyond the proximal end 128 of the first tubular member 120 and is operatively connected to the luer fitting 180. In this regard, reinforcement and axial support of the dilator 110, and specifically, the first tubular member 120 is enhanced as at least a portion of the axial forces applied on the luer fitting 180 to penetrate the distal end 112 of the dilator 110 through the tissue wall are translated directly into the second tubular member 142.

In another embodiment, the distal and proximal ends 112, 114 of the dilator 110 define a length of the dilator 110. The length ($l_D$) of the dilator 110 generally varies between about 5 centimeters and about 30 centimeters. The outer diameter of the dilator 110 is generally between about 4 french and about 24 french. A wall thickness ($t_D$) of the dilator, as defined by exterior surface 130 and the bore 150, may be between about 0.012 inches and about 0.136 inches. In addition, dilators 110 fabricated according to the principles of the present invention may have a 30° bending stiffness of at least about 0.2 lbs., and preferably, between about 0.2 lbs. and about 2.0 lbs., and may have a column strength of at least about 0.4 lbs., and preferably, between about 0.4 lbs. and about 2.5 lbs., and may have a resistance to buckling of at least about 0.2 lbs., and preferably between about 0.2 lbs. and about 2.5 lbs.

In another embodiment of the invention, illustrated in FIGS. 12–14, the above-described sheath 20 and dilator 110 may cooperate as a vessel access system below the skin line for dilating and/or penetrating an intravascular tissue wall 18 and for facilitating the introduction of a catheter (not shown) through the intravascular tissue wall 18. In this embodiment, in order to accommodate insertion of the sheath 20 and the dilator 110, a needle (not shown) may be inserted below the skin line 14 and into an intravascular tissue wall 18, thereby puncturing the intravascular tissue wall 18 by inserting a distal end of the needle through the intravascular tissue wall 18 (e.g., a vein or an artery). For purposes of guiding the sheath 20, dilator 110 and catheter (not shown) through the hole 16 and into and about the vein or artery, a distal end 72 of a guide wire 70 may be inserted through the hole 16 via the needle. The needle may be withdrawn from the hole 16 in the intravascular tissue wall 18.

The distal end 112 of the dilator 110 may be inserted into the proximal end 34 of the sheath 20, and specifically, through the hemostasis valve adapter 170 at the proximal end 34 of the sheath 20. In this regard, the outer diameter of the dilator 110 may slidably engage the lumen 38 of the sheath 20. As illustrated in FIG. 12, the distal end 112 of the dilator 110 (e.g., first tubular member 120) may be slid distally, below the skin line 14, toward and through the hole 16, in order to penetrate through any hardened (e.g., calcified) vessel regions within the intravascular tissue wall. In one embodiment, at least a portion of the dilator 110 having a reinforced portion is inserted through the hole 16 to enhance penetration of the sheath 20 through hardened tissue. In this regard, at least a portion of the reinforcing tube, and, in particular, a distal portion 144 of the second tubular member 142 positioned within the first tubular member 120 is positionable distal the hole 16 in the intravascular tissue wall 18. Providing reinforcement at the distal portion 124 of the first tubular member 120 with the second tubular member 142 (e.g., reinforcing member) enhances penetration of the distal portion 124 through hardened (e.g., calcified) regions of the tissue since the second tubular member 142 provides increased column strength (e.g., of at least about 0.2 lbs.) and resistance to buckling. In one embodiment, a ratio of the outer diameters of the first tubular member 120 to second tubular member 142 (e.g., reinforcing member) is less than about 7.25.

After penetrating through any hardened tissue and dilating the hole 16, the distal end 30 of the introducer sheath 20 may then be introduced (e.g., inserted) through the hole 16, as shown in FIGS. 13–14. In one embodiment, where the sheath 20 comprises a wire braid 50 which extends into the portion 32 of the tubular member 26, as illustrated in FIGS. 12–14, a portion of the wire braid 50 may thereby be extended below the skin line 14 and through the intravascular tissue wall 18. Reinforcing the tubular member 26 in the tapered portion 32 with the wire braid 50 enhances and facilitates introduction of the distal end 30 of the sheath 20 since buckling is substantially inhibited and column strength is increased. The dilator 110 may be withdrawn from the sheath 10 and a catheter (not shown) may be introduced into the hole 16 via the sheath 20 and the guide wire 70.

It should be noted that although the wire braid 50 and second tubular member 142 provide increased column strength and resistance to buckling to the sheath 20 and to the dilator 110, respectively, the sheath 20 and dilator 110 are nevertheless flexible enough to generally follow the guide wire 70, which traces a path governed by the procedure to be performed and the configuration and curvature of the vein or artery. Thus, as axially directed forces are applied on at least one of the dilator and sheath to push the distal portions 28, 113 of the sheath 20 and dilator 110, respectively, into the incision 16 and along the guide wire 70, at least the distal portions 28, 113 bend to follow the guide wire 70. As such, flexibility in the distal portions 28, 113 of the sheath 20 and dilator 110, respectively, substantially inhibit damage to the intravascular tissue walls. In this regard, as the distal ends 30, 112 of the sheath 20 and dilator 110, respectively, slidably engage and follow the curvature of the guide wire 70, at least a portion of the sheath 20 and the dilator 110 curve or bend with the guide wire 70, and therefore curve about the vein or artery, as defined by the walls 18, therewith. In one embodiment, where the wire braid 50 extends into the distal portion 28 of the sheath 20, at least the distal portion 28 of the sheath 20 is flexible such that the sheath 20 slidably engages the guide wire 70 and is bendable about the guide wire 70. In another embodiment, where the second tubular member 142 (e.g., reinforcing member) extends into the distal portion 124 of the first tubular member 120 of the dilator 110, at least the distal portion 113 of the dilator 110 slidably engages the guide wire 70 and is bendable about the guide wire 70.

The wire braid 50 may comprise at least two intertwined wires, wherein a first of the wires is wound clockwise about the sheath 20 and a second of the wires is wound counterclockwise about the sheath 20. In this regard, the sheath 20 may have a column strength of at least about 0.2 lbs. and a 30° bending stiffness of at least about 0.2 lbs. In this embodiment, the outer diameters of the sheath 20 and the dilator 110 define a first ratio which is less than about 1.20. In a preferred embodiment, the first ratio is between about 1.04 and about 1.20. Furthermore, and as illustrated in FIGS. 12–14, the dilator 110 may be tubular in configuration, such that a second ratio of the inner diameter of the sheath 20, as defined by the lumen 38 extending therethrough, to the outer diameter of the dilator 110, as defined by the outer wall of the first tubular member 120, is less than about 1.06.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A sheath for use in introducing a catheter into an incision in an intravascular tissue wall of a patient, said sheath comprising:

a tubular member having distal and proximal ends and defining a lumen extending therebetween for receiving and guiding the catheter into the incision, said distal end of said tubular member being positionable through the incision in the tissue wall; and a wire braid positioned about at least said distal end of said tubular member for reinforcing said distal end of said tubular member, said wire braid comprising at least two wires, wherein said wires are intertwined;

wherein said sheath has a column strength of at least about 0.2 lbs. and a 30° bending stiffness of at least about 0.2 lbs.

2. A sheath, as claimed in claim 1, wherein a first of said wires is wound clockwise about said distal end of said tubular member and a second of said wires is wound counterclockwise about said distal end of said tubular member.

3. A sheath, as claimed in claim 1, wherein at least a first of said wires overlays at least a second of said wires at a first position about said tubular member and underlays said second of said wires at a second position about said tubular member.

4. A sheath, as claimed in claim 1, wherein said wire braid comprises at least 8 wires.

5. A sheath, as claimed in claim 1, wherein said wire braid has a density of at least 5 pic/inch.

6. A sheath, as claimed in claim 1, wherein said wire braid is positioned within said tubular member, substantially between an exterior surface of said tubular member and said lumen.

7. A sheath, as claimed in claim 1, wherein said wires comprise a material selected from the group consisting of stainless steel, carbon fiber, aramid fiber, polymers and metal.

8. A sheath, as claimed in claim 1, wherein a dimension of each of said wires is between about 0.0005 inches and about 0.010 inches.

9. A sheath, as claimed in claim 1, wherein a wall thickness of said tubular member is defined by said lumen and an exterior surface of said tubular member.

10. A sheath, as claimed in claim 9, wherein said wall thickness of said tubular member is less than about 0.007 inches.

11. A sheath, as claimed in claim 9, wherein the ratio of an outer diameter of said tubular member, defined by said exterior surface, to an inner diameter of said tubular member, defined by said lumen, defines a first ratio, wherein said first ratio is less than about 1.10.

12. A sheath, as claimed in claim 1, wherein said tubular member comprises a polymer.

13. A sheath for use in introducing a catheter through an incision in an intravascular tissue wall of a patient, said sheath comprising:

tubular means, for receiving and guiding the catheter through the incision in the tissue wall, said tubular means having distal and proximal ends and defining a lumen extending therebetween, wherein said distal end of said tubular means is positionable through the incision in the tissue wall, wherein said tubular means has a column strength of at least about 0.2 lbs and a 30° bending stiffness of at least about 0.2 lbs and wherein a wall thickness of said tubular means is defined by an exterior surface of said tubular means and said lumen, wherein said wall thickness is between about 0.001 inches and about 0.007 inches.

14. A sheath, as claimed in claim 13, wherein said column strength is between about 0.4 lbs. and about 2.5 lbs.

15. A sheath, as claimed in claim 13, wherein said tubular means comprises a tubular member and a wire braid positioned about said tubular member, said braid comprising at least two wires, wherein said wires are intertwined.

16. A dilator for use in penetrating through an incision in an intravascular tissue wall of a patient, said dilator comprising:

a first tubular member having distal and proximal portions and defining a lumen extending therebetween, said distal portion being positionable through the incision in the tissue wall; and a reinforcing member positionable within said first tubular member, said reinforcing member extending between said distal and proximal portions of said first tubular member to provide axial support to said first tubular member, wherein at least a part of said distal portion of said reinforcing member is positionable through the incision in the tissue wall, wherein said dilator has a 30° bending stiffness of at least about 0.2 lbs. and a column strength of at least about 0.4 lbs.

17. A dilator, as claimed in claim 16, wherein a wall thickness of said first tubular member is defined by an exterior surface of said first tubular member and said lumen, wherein said reinforcing member comprises a second tubular member defining a bore extending therethrough and includes a wall thickness defined by said bore and an exterior surface of said reinforcing member, wherein the ratio of said wall thicknesses of said first tubular member and said reinforcing member is between about 2.0 and about 90.

18. A dilator, as claimed in claim 17, wherein said first tubular member comprise a polymer.

19. A dilator, as claimed in claim 16, wherein said distal portion of said first tubular member comprises a tapered section having distal and proximal portions, wherein the taper from said distal portion to said proximal portion of said tapered section is between about 1° and about 10°.

20. A dilator, as claimed in claim 19, wherein a distal end of said reinforcing member extends into said tapered section of said first tubular member, substantially between said distal and proximal portions of said tapered section.

21. A dilator, as claimed in claim 19, wherein a distal end of said reinforcing member extends up to said distal portion of said tapered section of said first tubular member.

22. A dilator, as claimed in claim 19, wherein a distal end of said reinforcing member extends proximal to said distal portion of said tapered section.

23. A dilator, as claimed in claim 17, wherein a wall thickness of said first tubular member is defined by an exterior surface of said first tubular member and said lumen, said wall thickness being less than about 0.1345 inches.

24. A dilator, as claimed in claim 17, wherein said reinforcing member further comprises a material selected from the group consisting of stainless steel, polymer composites, liquid crystal polymer and metal alloys.

25. A dilator, as claimed in claim 17, wherein said reinforcing member comprises a second tubular member defining a bore extending therethrough and includes a wall thickness defined by said bore and an exterior surface of said reinforcing member, wherein said reinforcing member has a wall thickness of greater than about 0.0005 inches.

26. A dilator, as claimed in claim 17, further comprising a luer fitting for applying an inserting force to move said dilator through said tissue wall, wherein said luer fitting is connected to a proximal end of at least one of said first tubular and reinforcing members.

27. A dilator for use in penetrating through hardened regions about an incision in an intravascular tissue wall of a patient, said dilator comprising:

tubular means having distal and proximal portions and defining a bore extending therethrough, wherein said distal portion is positionable through the hardened regions of the tissue wall, wherein said tubular means has a column strength of at least about 0.2 lbs. and a 30° bending stiffness of at least about 0.2 lbs.

28. A dilator, as claimed in claim 27, wherein a wall thickness of said tubular means is defined by an exterior surface of said tubular means and said bore, wherein said wall thickness is between about 0.012 inches and about 0.140 inches.

29. A dilator, as claimed in claim 27, wherein said column strength is at least between about 0.2 lbs. and about 2.5 lbs.

30. A dilator, as claimed in claim 27, wherein said tubular means comprises a first tubular member and a reinforcing member positioned within a lumen defined by said first tubular member.

31. A vascular access system for use in penetrating through an incision in an intravascular tissue wall of a patient and facilitating the introduction of a catheter into the tissue wall via the incision, said system comprising:

a sheath;

a dilator for guiding said sheath through the incision in the tissue wall, said sheath and said dilator each having distal and proximal portions, wherein said distal portion of said dilator is positionable through the incision in the tissue wall to guide said distal portion of said sheath through the incision, wherein said sheath comprises a first tubular member defining a lumen there through for receiving said dilator, wherein exterior surfaces of said sheath and said dilator define outer diameters of said sheath and said dilator, respectively, wherein a first ratio of said outer diameter of said sheath to said outer diameter of said dilator is less than about 1.20 and wherein said sheath further comprises a wire braid positioned about at least a segment of said first tubular member for reinforcing said first tubular member, said wire braid comprising at least two wires, wherein said wires are intertwined;

wherein said sheath has a column strength of at least about 0.2 lbs. and a 30° bending stiffness of at least about 0.2 lbs.

32. A vascular access system, as claimed in claim 31, wherein said first ratio is between about 1.04 and about 1.20.

33. A vascular access system, as claimed in claim 31, wherein said dilator comprises a second tubular member, wherein a second ratio of an inner diameter of said sheath defined by said lumen to said outer diameter of said dilator is less than about 1.06.

34. A vascular access system, as claimed in claim 31, wherein said wire braid is wound about said segment of said first tubular member, between said exterior surface and said lumen of said first tubular member.

35. A vascular access system, as claimed in claim 31, wherein a first of said wires is wound clockwise about said segment of said first tubular member and a second of said wires is wound counterclockwise about said segment of said first tubular member.

36. A vascular access system, as claimed in claim 31, further comprising a reinforcing member, wherein said dilator comprises a second tubular member defining a bore therethrough for receiving said reinforcing member therein, said reinforcing member being positionable within said second tubular member to provide axial support to said second tubular member, wherein said reinforcing member comprises a third tubular member.

37. A vascular access system, as claimed in claim 36, wherein an exterior surface of said third tubular member defines an outer diameter of said reinforcing member, wherein said exterior surface of said dilator defines an outer diameter of said second tubular member, wherein a third ratio of said outer diameter of said second tubular member to said outer diameter of said reinforcing member is less than about 7.25.

38. A vascular access system, as claimed in claim 31, wherein said dilator has a column strength of at least about 0.2 lbs.

39. A method for dilating an incision in an intravascular tissue wall, said method comprising the steps of:
   positioning a distal portion of a dilator through the incision, distal the intravascular tissue wall, to dilate the incision; and
   positioning a distal portion of an introducer sheath through the incision, distal the intravascular tissue wall, the introducer sheath comprising a first tubular member defining a lumen extending therethrough and wherein said introducer sheath has a column strength of at least about 0.2 lbs. and a 30° bending stiffness of at least about 0.2 lbs., wherein said step of positioning the distal portion of the sheath comprises advancing a distal portion of a wire braid wound about the first tubular member through the incision, the wire braid comprising at least two intertwined wires.

40. A method, as claimed in claim 39, wherein a first of the intertwined wires is wound about the first tubular member in a clockwise direction and a second of the intertwined wires is wound about the first tubular member in a counterclockwise direction.

41. A method, as claimed in claim 39, wherein at least a first of the intertwined wires overlays at least a second of the intertwined wires at a first position about the first tubular member and underlays the second of the intertwined wires at a second position about the first tubular member.

42. A method, as claimed in claim 39, wherein the dilator comprises a second tubular member having distal and proximal portions and a reinforcing member positioned about the second tubular member and extending into the distal portion of the second tubular member, wherein said step of positioning the distal portion of the dilator comprises the step of advancing a distal portion of the reinforcing member through the incision, distal the intravascular tissue wall.

43. A method, as claimed in claim 39, further comprising the step of inserting a distal end of a guide wire through the incision, wherein said steps of positioning the distal portions of the sheath and dilator through the incision comprise the step of advancing at least the distal portions of the sheath and dilator over the guide wire, toward the distal end of the guide wire.

44. A method, as claimed in claim 43, wherein said step of advancing the distal portions of the sheath and dilator comprises the step of applying an axially directed force toward the incision on at least one of the sheath and dilator.

45. A method, as claimed in claim 44, wherein said step of advancing further comprises the step of slidably engaging the distal portion of the dilator with the guide wire to bend at least the distal portions of the sheath and dilator to follow the guide wire distal the skin line.

46. A vascular access system for use in penetrating through an incision in an intravascular tissue wall of a patient and facilitating the introduction of a catheter into the tissue wall via the incision, said system comprising:
   a sheath;
   a dilator for guiding said sheath through the incision in the tissue wall, said sheath and said dilator each having distal and proximal portions, wherein said distal portion of said dilator is positionable through the incision in the tissue wall to guide said distal portion of said sheath through the incision, wherein said sheath comprises a first tubular member defining a lumen therethrough for receiving said dilator, wherein exterior surfaces of said sheath and said dilator define outer diameters of said sheath and said dilator, respectively, wherein a first ratio of said outer diameter of said sheath to said outer diameter of said dilator is less than about 1.20 and wherein said sheath has a column strength of at least about 0.2 lbs. and a 30° bending stiffness of at least about 0.2 lbs.

\* \* \* \* \*

UNITED STATES PATENT AND TRADEMARK OFFICE
CERTIFICATE OF CORRECTION

PATENT NO. : 6,053,904
DATED : 04/25/00
INVENTORS : Scribner et al.

It is certified that error appears in the above-identified patent and that said Letters Patent are hereby corrected as shown below:

On the cover page of the patent at [75] Inventors:, please change "4697 Quail Creek La., Boulder, Colo. 80301" to -- 1960 Colleen Dr., Los Altos, Calif. 94024 --.

Signed and Sealed this

Third Day of April, 2001

NICHOLAS P. GODICI

*Attest:*

*Attesting Officer*     Acting Director of the United States Patent and Trademark Office